United States Patent [19]

Kakino

[11] Patent Number: 4,478,538
[45] Date of Patent: Oct. 23, 1984

[54] DEVICE FOR DETECTING TOOL ABNORMALITY

[75] Inventor: Yoshiaki Kakino, 256-5, Iwakura Hanazono-cho, Sakyo-ku, Kyoto-Shi, Japan

[73] Assignees: Yoshiaki Kakino, Kyoto; NF Circuit Design Block Co., Ltd., Yokohama; Showa Tool Co., Ltd., Toyonaka, all of Japan

[21] Appl. No.: 426,244

[22] Filed: Sep. 28, 1982

[30] Foreign Application Priority Data

Apr. 23, 1982 [JP] Japan .................. 57-69354

[51] Int. Cl.³ .............. G01N 3/58; G08B 21/00; B23B 49/00
[52] U.S. Cl. ............................ 408/6; 408/9; 408/11; 73/104; 340/683; 409/134; 409/194
[58] Field of Search .............. 73/104; 340/683; 408/6, 408/9, 11; 409/134, 187, 194

[56] References Cited

U.S. PATENT DOCUMENTS

| 2,774,261 | 12/1956 | Leibing | 408/9 |
|---|---|---|---|
| 3,713,127 | 6/1973 | Keledy et al. | 73/587 |
| 3,793,627 | 2/1974 | Darrel et al. | 73/104 X |
| 3,816,015 | 6/1974 | Bilz et al. | 408/6 |
| 3,841,149 | 10/1974 | Edwin et al. | 73/104 X |
| 3,989,405 | 11/1976 | Quackenbush | 408/11 |
| 4,087,801 | 5/1978 | Noh | 73/104 X |
| 4,090,802 | 5/1978 | Bilz | 408/6 |
| 4,220,995 | 9/1980 | Shoda | 73/104 X |
| 4,233,600 | 11/1980 | Rogers et al. | 340/683 |
| 4,237,454 | 12/1980 | Meyer | 340/683 X |
| 4,332,161 | 6/1982 | Kakino | 73/104 |
| 4,342,528 | 8/1982 | Nozu et al. | 408/6 |

FOREIGN PATENT DOCUMENTS

| 2101704 | 8/1972 | Fed. Rep. of Germany | 408/11 |
|---|---|---|---|
| 1391176 | 4/1975 | United Kingdom | 408/6 |
| 572376 | 9/1977 | U.S.S.R. | 408/6 |
| 674839 | 6/1979 | U.S.S.R. | 408/6 |
| 703251 | 12/1979 | U.S.S.R. | 408/9 |

Primary Examiner—Gerald Goldberg
Assistant Examiner—Tom Noland
Attorney, Agent, or Firm—Frishauf, Holtz, Goodman and Woodward

[57] ABSTRACT

When a drill is overloaded, while cutting a hole in a workpiece, a torque limiter disconnects the drill from a main spindle. As the drill is disconnected from the main spindle, the torque limiter generates high-level elastic waves. The elastic waves are converted by a transducer into a voltage signal. The level of the voltage signal is compared with a threshold value.

7 Claims, 9 Drawing Figures

DEVICE FOR DETECTING TOOL ABNORMALITY

BACKGROUND OF THE INVENTION

The present invention relates to a device for detecting that a rotary cutter such as a drill, a tap or an end mill is in an abnormal state and is likely to break unless its rotation is stopped, and for detecting that the end of the life of the cutter is approaching.

As the technology of production advances, it is increasingly demanded that less manpower or no manpower be used in operating machine tools. In order to achieve a semi-automatic or a full automatic machining an in-process detection of tool abnormality such as damage to, or breakage of, a cutting tool must be performed.

An in-process detection method is known which is effective in detecting tool abnormality such as damage to, or breakage of, a rotary cutter. The method comprises the steps of detecting an acoustic emission from a rotary cutter which occurs when the rotary cutter is damaged or broken, generating a signal representing the acoustic emission, and giving an alarm according to the signal. The signal has so high a level that it can be used in the in-process detection of such tool abnormality. The method is disadvantageous, however. The tool abnormality cannot be detected before the tool is damaged or broken. If a rotary cutter is broken while cutting a workpiece, a fragment remains in the workpiece. In order to further cut the workpiece, the fragment must be pulled out, which would take much time and labor. What is more, the fragment may damage the workpiece as it is pulled out, thus leaving a defective product. Consequently, the yield of products may be reduced and the cost of products may rise.

Another in-process detection method is known for predicting the damage to, or breakage of, a drill. The method utilizes a variation in load current of a motor which rotates the drill. The variation of load current is, however, small when the drill has a diameter of 7 mm or less. The method does not well work in predicting the damage to, or breakage of, a drill which is 7 mm or less thick.

Still another in-process detection method is proposed for predicting the damage to, or breakage of, a drill. In this method a strain gauge is attached to a spindle. As the drill is loaded, the spindle driving the drill is gradually strained. The strain gauge detects the strain of the spindle, thereby predicting the damage to, or breakage of, a drill. The load applied on a drill of a small diameter is small, and the method cannot precisely predict the damage to, or breakage of, a drill of a small diameter.

As mentioned above, no method has been proposed that is effective in predicting and thus preventing the damage to, or breakage of, a rotary cutter, particularly a drill having a small diameter. If an automatic machining is to be performed using a machine tool such as a machining center, use of small-diameter rotary cutters has to be avoided.

SUMMARY OF THE INVENTION

Accordingly, the object of the invention is to provide a device for detecting tool abnormality, which can predict damage to, or breakage of, small-diameter tools and which can detect the approach of the end of tool life.

A device for detecting tool abnormality according to the invention comprises a means for generating elastic waves. The means is installed in a tool holder or a spindle. When a cutter attached to the tool holder or spindle receives an excessive load while cutting a workpiece and is thus likely to break, the means generates elastic waves in response to the excessive load. The elastic waves generated by the means are converted into an electric signal by a transducer attached to, for example, the spindle head. The signal is supplied to a detector which discriminates the signal from noise resulting from the machining, thereby generating an output signal. In response to the output signal from the detector, an alarm is given. Whenever an alarm is given, cutting is stopped and the tool is inspected, and it is replaced by a new one, if necessary.

According to the invention, a means which generates high-level elastic waves when a tool receives an excessive load and is likely to break may be used. In this case the device of the present invention can predict the breakage of a tool even if the tool has a small diameter.

Further, according to the invention, a means which generates elastic waves in response to a specific load which acts on a tool which is worn out may be used. In this case, the device of the invention can detect that the end of the tool life is approaching.

DETAILED DESCRIPTION OF THE PREFERRED EMBODIMENTS

A few embodiments of the invention will be described in detail with reference to the accompanying drawings.

Figure 1:
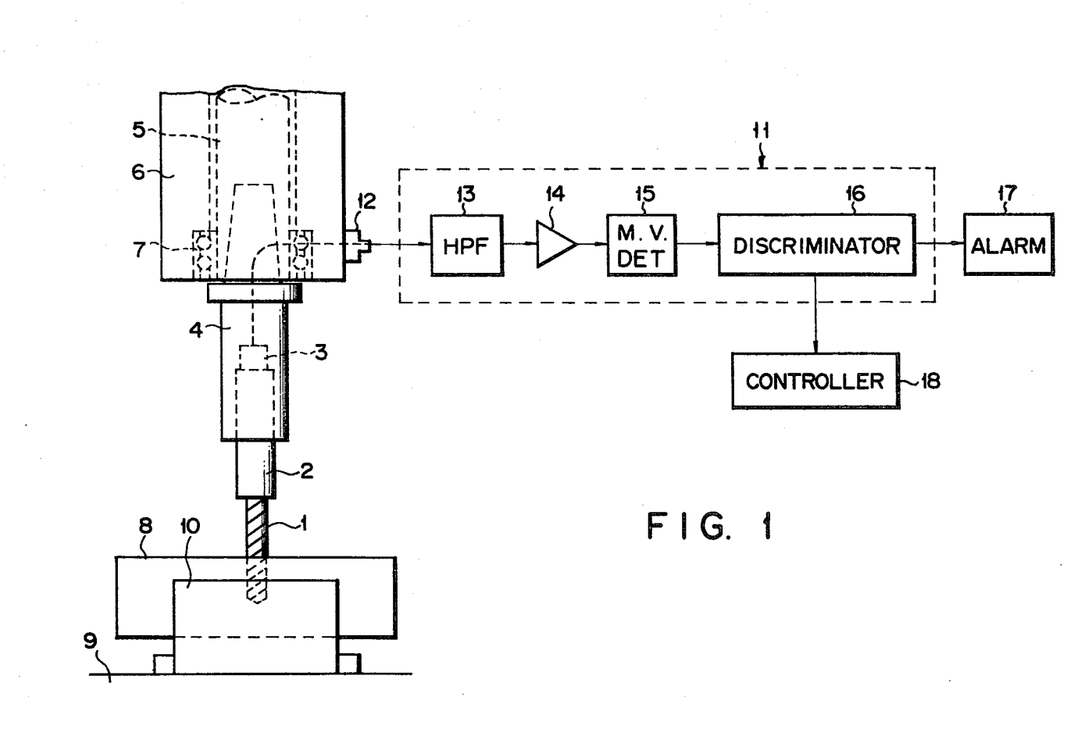
FIG. 1 is a block diagram of a device according to the invention.

As shown in FIG. 1, a drill 1, or a rotary cutter, is held by a tool holder 2. A torque limiter 3 is attached to the rear end of the tool holder 2. The rear end portion of the tool holder 2 and the torque limiter 3 are disposed in a tooling section 4. The tooling section 4 is detachably coupled to a spindle 5 of a machine tool. The rotation of the spindle 5 can thus be transmitted to the drill 1. The spindle 5 is supported rotatable on a ball bearing 7 which is provided in a spindle head 6. When rotated, the drill can cut a hole in a workpiece 8 clamped by a vice 10 which is fixed on a table 9.

A detecting circuit 11 is connected to a piezoelectric transducer 12 which is fixed to the outer surface of the spindle head 6. The transducer 12 detects every vibration the spindle head 6 undergoes while the drill 1 is cutting a hole in the workpiece 8 and converts the vibration into an electric signal. The output signal from the transducer 12 is supplied to a high-pass filter 13 of the detecting circuit 11. Only the high-frequency component of the signal is thus taken out. The output signal from the high-pass filter 13 is amplified by an amplifier 14 and then supplied to a mean value detector 15. The detector 15 is an integrator and generates a DC voltage signal which corresponds to the mean level of its input signal. The DC voltage signal is supplied to an amplitude discriminator 16. The amplitude discriminator 16 compares the level of the DC voltage signal with a predetermined reference level and generates a signal representing the difference between the levels compared. The output signal from the amplitude discriminator 16 is supplied, if necessary, to an alarm generator 17 and a controller 18. The controller 18 is installed in the machine tool as in most cases. In response to the output from the amplitude discriminator 16 it moves the drill 1 away from the workpiece 8 and, if necessary, replaces the drill 1 by a new one or a drill of another kind. The controller 18 is of the well-known type and is not described here in detail.

Figure 2:
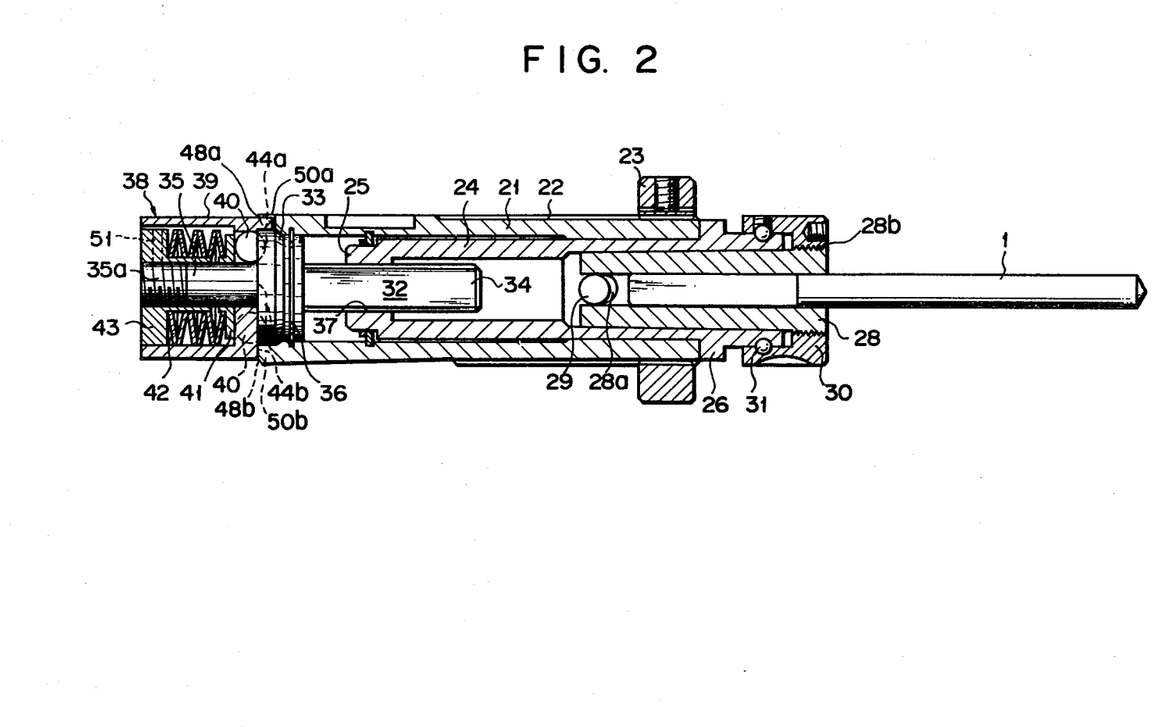
FIG. 2 is a vertical sectional view of the tooling section of the device shown in FIG. 1.
Figure 3:
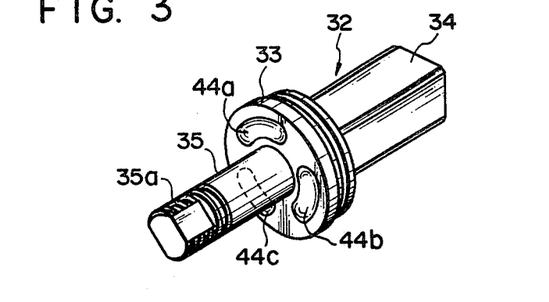
FIG. 3 is a perspective view of a driver used in the tooling section shown in FIG. 2.
Figure 4:
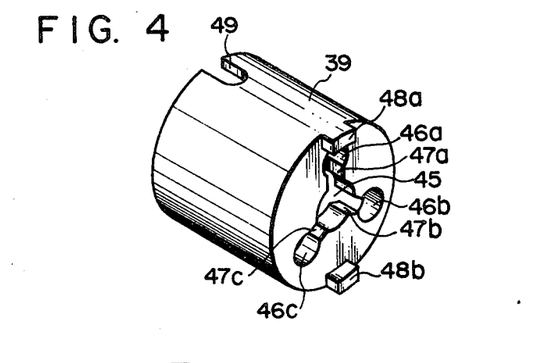
FIG. 4 is a perspective view of a retainer, or the main body of a torque limiter shown in FIG. 2.

With reference to FIGS. 2 to 4, the tool holder 2, torque limiter 3 and tooling section 4—all shown in FIG. 1—will be described.

As shown in FIG. 2, the tool holder 2 comprises a hollow cylinder 21, or a main body. A thread 22 is machined in the outer periphery of the front end portion of the cylinder 21. A lock nut 23 is threaded on the front end portion of the cylinder 21. A drill spindle 24 is partly inserted in the cylinder 21. The drill spindle 24 is a hollow cylinder which has a bottom 25 at the rear end. The bottom 25 has a polygonal hole 37. A flange 26 is formed integral with the front end portion of the drill spindle 24 which is protruding from the hollow cylinder 21. Hence, the drill spindle can move into the hollow cylinder 21 until the flange 26 abuts on the front end of the hollow cylinder 21.

The front end portion of the drill spindle 24 has a hole whose diameter increases gradually toward the front end of the drill spindle 24. A conical collet 28 is inserted in this hole. A U-notch 28a is machined in the rear end of the collet 28. Put in the U-notch 28a is drive pin 29 which pierces the drill spindle 24 and which extends in the radial direction thereof. A thread 28b is machined in the outer periphery of the front end portion of the collet 28. On the thread 28b a clamp nut 30 is threaded for rotatably supporting the drill spindle 24 through a ball bearing 31. The clamp nut 30 fixes the rear end of the drill 1 to the collet 28.

In the rear end portion of the hollow cylinder 21 a driver 32 is disposed for transmitting the rotation of the hollow cylinder 21 to the drill spindle 24. The driver 32 comprises a disc 33 which is detachably held in the hollow cylinder 21 by means of a snap ring 36, a polygonal shaft 34 connected to one side of the disc 33. The polygonal shaft 34 is fitted in the polygonal hole 37 of the bottom 25 of the drill spindle 24.

The shaft 35 of the driver 32 is connected to the torque limiter 3. The torque limiter 3 therefore transmits the rotation of the main spindle 5 to the driver 32. As shown in FIGS. 3 and 4, the torque limiter 3 comprises a retainer 39, or a main body, three balls 40, a guide bush 41 movably mounted on the shaft 35 of the driver 32, coned disc springs 42 put in face-to-face relation, each opposing the adjacent one and a spring force adjusting nut 43. The balls 40 are inserted in three arcuate recesses 44a, 44b and 44c, respectively, which are machined in one surface of the disc 33 of the driver 33 and which are spaced 120° apart. A thread 35a is machined in the periphery of the free end portion of the shaft 35. The spring force adjusting nut 43 is threaded on the thread 35a. The arcuate recesses 44a, 44b and 44c are arranged in a circle around the axis of the shaft 35.

The retainer 39 is a bottomed hollow cylinder as shown in FIG. 4. The bottom of the retainer 39 has an opening 45 which is coaxial with the retainer and three holes 46a, 46b and 46c which are located around the opening 45 and which are spaced 120° apart. Three slits 47a, 47b and 47c are machined in the bottom. The slit 47a connects the opening 45 to the hole 46a, the slit 47b connects the opening 45 to the hole 46b, and slit 47c connects the opening 45 to the hole 46c. The holes 47a, 47b and 47c receive the three balls 40, respectively. Two transmission projections 48a and 48b protrude from the front end of the retainer 39. These projections 48a and 48b are fitted in recesses 50a and 50b which are machined in the inner periphery of the rear end portion of the hollow cylinder 21 of the tool holder 2 as shown in FIG. 2. A U-notch 49 is cut in the rear end of the retainer 39. Through the U-notch 49 a pin 51 (shown in FIG. 2) extends into a hole made in the spring force adjusting nut 43, thereby preventing the nut 43 from rotating. The force of the coned disc springs 42 is adjusted so that the torque limiter operates in response to a specific load which acts on the drill when the end of the life of the drill approaches.

The hollow cylinder 21 is fixed in the tooling section 5. In other words, the tool holder 2 is fixed in the tooling section 4. When the main spindle 5 is rotated and the drill 1 is pressed against the workpiece 8, the drill 1 cuts a hole in the workpiece 8. A chip-jamming or a blade-fusing may occur during the cutting. In case it happens, the drill 1 is overloaded and the balls 40 come out of the arcuate recesses 44a, 44b and 44c, overcoming the force of the coned disc springs 42. At this time, torque can hardly be transmitted from the hollow cylinder 21 to the driver 32. As a result, the load applied on the drill 1 decreases very much. Subsequently the hollow cylinder 21 is rotated. The balls 40 are then moved into the arcuate recesses 44a, 44b and 44c. The torque is then transmitted again from the hollow cylinder 21 to the driver 32, and the drill 1 is no longer overloaded. The normal cutting is thus performed by the drill 1. If the drill 1 remains overloaded even after the torque transmission has been resumed, the balls 40 repeatedly come out of and into the recesses 44a, 44b and 44c. As long as this movement of the balls 40 is repeated, a torque smaller than a predetermined value is transmitted to the drill 1.

Every time the balls 40 are pressed against the disc 33 with a great force, a large sound is made. The sound is elastic waves containing ultrasonic waves. The elastic waves are transmitted to the spindle head 6 through the tooling section 4 and then through the ball bearing 7. They finally reach the transducer 12. Upon receipt of the elastic waves the transducer 12 generates an electric signal. The noise or vibration of the drill 1, tool holder 2, tooling section 4 and ball bearing 7 as well as the elastic waves from the torque limiter 38 is transmitted to the transducer 12. The noise should be removed to thereby provide an electric signal which corresponds solely to the elastic waves from the torque limiter 38. For this purpose, the output signal from the transducer 12 is supplied to the high-pass filter 13, which removes the noise component of the signal from the transducer 12. The output signal from the high-pass filter 13 is amplified by the amplifier 14. The output signal from the amplifier 14 is supplied to the mean value detector 15, which generates an output signal.

When the output signal from the mean value detector 15 surpasses a threshold value set to the amplitude discriminator 16, the discriminator 16 generates a signal. The signal from the discriminator 16 is supplied to the alarm generator 17 and the controller 18. The alarm generator 17 then produces an alarm, and at the same time the controller 18 generates an instruction signal. According to the instruction signal the spindle head 6 is moved up until the rotating drill 1 leaves the workpiece 8, whereby the cutting is stopped. Upon lapse of a predetermined time, the controller 18 generates another instruction signal. According to this instruction signal, the spindle head 6 is moved down until the rotating drill 1 comes into contact with the workpiece 8, whereby the cutting is resumed. If the drill 1 is found still overloaded, the controller 18 generates an instruction signal, thus moving up the spindle head 6, and then generates another instruction signal upon lapse of the predetermined time, thereby moving down the spindle head 6. The cycle is repeated. If the drill 1 is found still overloaded after the cycle has been repeated a certain number of times, the end of life of the drill 1 is considered approaching. In this case, the controller 18 generates an instruction signal, thereby stopping the rotation of the drill 1 and thus replacing the drill 1 by a new one.

Figure 5:
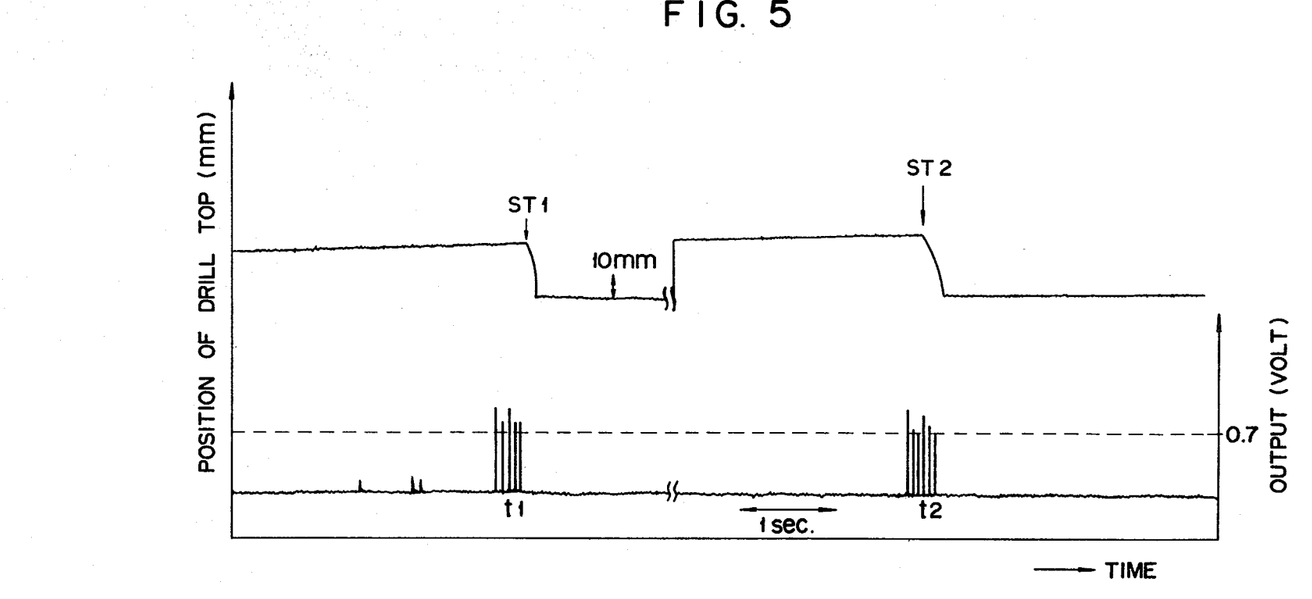
FIG. 5 is a timing chart illustrating how a cutter is controlled by the device shown in FIGS. 1-4.

FIG. 5 is a timing chart illustrating how a drill was controlled by the device shown in FIGS. 1-4. The drill used was made of steel SKH4 (JIS) and 5 mm in diameter. The workpiece used was made of hardened carbon steel S45C (JIS) having a hardness (HRC) of 26. The main spindle was rotated at 500 rpm and fed at 100 mm/min. The high-pass filter used had a cutoff frequency of 100 KHz. The gain of the amplifier used was 62 dB. The threshold value set to the amplitude discriminator was 0.7 V. The reference torque set to the torque limiter was 0.2 Kg·cm.

The drill 1 was rotated and pressed against the workpiece 8, thus cutting a hole in the workpiece 8. At time $t_1$ the torque limiter 3 continuously operated, and the level of the input signal to the amplitude discriminator 16 surpassed 0.7 V. As a result, the alarm generator 17 produced an alarm. At the same time, the controller 18 generated an instruction signal, whereby the spindle head 6 was moved upward for the first time (first step ST1). Upon lapse of a predetermined time, the spindle head 6 is moved down, thus resuming the cutting. At time $t_2$ the torque limiter 3 continuously operated for the second time. Thus, the spindle head 6 was moved upward for the second time (second step ST2). The spindle head 6 was quickly moved up every time an excessive load was applied on the drill 1. Accordingly, the breakage of the drill 1 was prevented.

Figure 6:
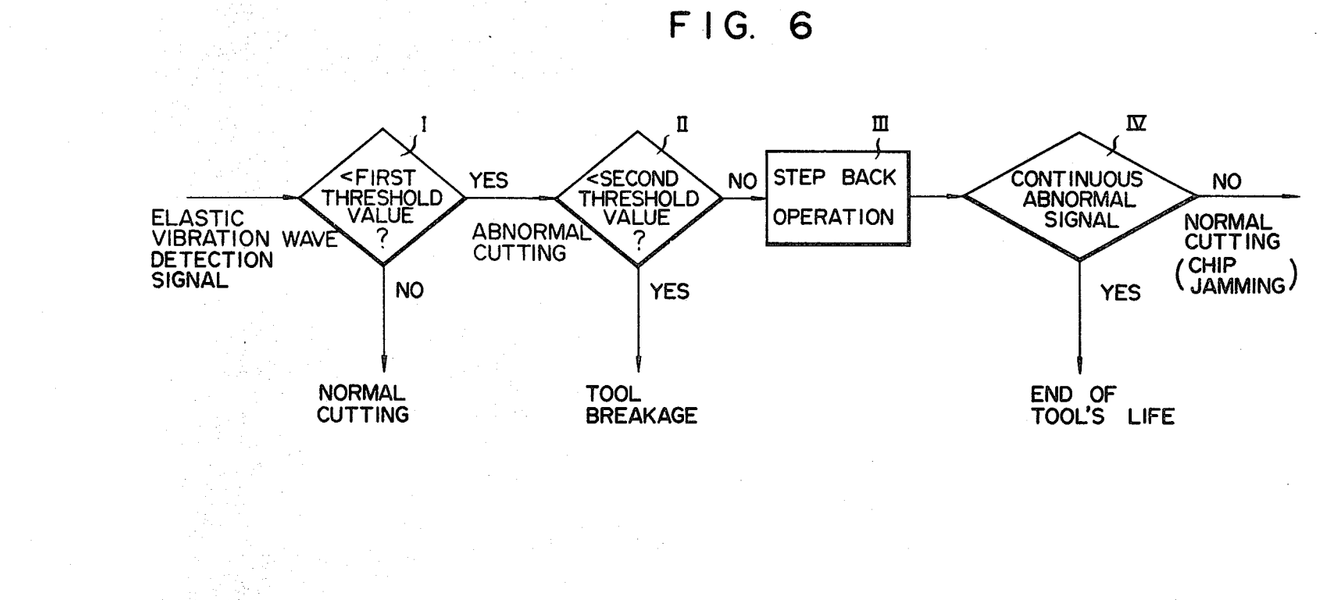
FIG. 6 is a flow chart illustrating the operation of the device shown in FIGS. 1-4.

If the spindle head 6 is moved up several times after time $t_2$ within a specific period of time, the end of life of the drill 1 is considered approaching and the controller 18 generates an instruction signal to stop the rotation of the drill and to replace the drill with a new one. FIG. 6 is a flow chart illustrating how the controller 18 generates various instruction signals.

Figure 7:
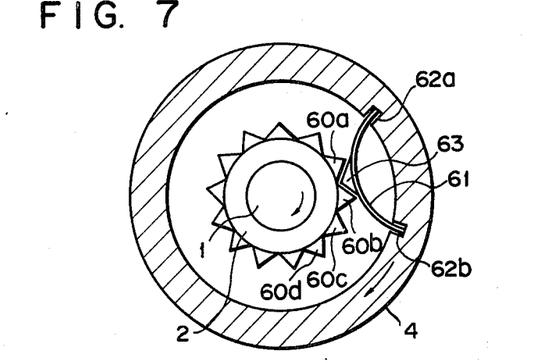
FIGS. 7, 8A and 8B schematically show torque limiters which are used in other devices according to the invention.

The device described above is applied to a drill. Nonetheless it can be applied to other rotary cutters such as a tap or an end mill. Further, the torque limiter 3 may be replaced by any torque limiter that can generate high-level elastic waves whenever the rotary cutter is overloaded. It may therefore be replaced by such a ratchet type torque limiter as shown in FIG. 7. If the ratchet type torque limiter is used, triangular teeth 60a, 60b, 60c, . . . are formed on the outer periphery of the tool holder 2, and a curved leaf spring 61 with a triangular ratchet 63 is fixed to the inner periphery of the tooling section 4, with both ends inserted in grooves 62a and 62b, respectively, which are cut in the inner periphery of the tooling section 4. The triangular ratchet 63 lies in a gap between, for example, the adjacent triangular teeth 60a and 60b as long as a normal load is applied on the drill 1. In this condition, as the tooling section 4 rotates in the direction of arrow (FIG. 7), both the tool holder 2 and the drill 1 rotate in the same direction. When the drill 1 is overloaded, the ratchet 63 rides onto the triangular tooth 60b and slips into the gap between the teeth 60b and 60c. As long as the drill 1 remained overloaded, the ratchet 63 further slips into the gap between the teeth 60c and 60d, the gap between the teeth 60d and 60e, the gap between the teeth 60e and 60f, and so forth. The leaf spring 61 is thus vibrated and generates high-level elastic waves. The elastic waves are converted by the transducer 12 into an electric signal.

Figure 8A:
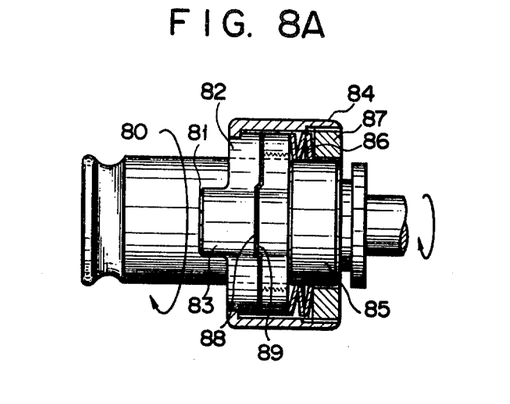
Figure 8B:
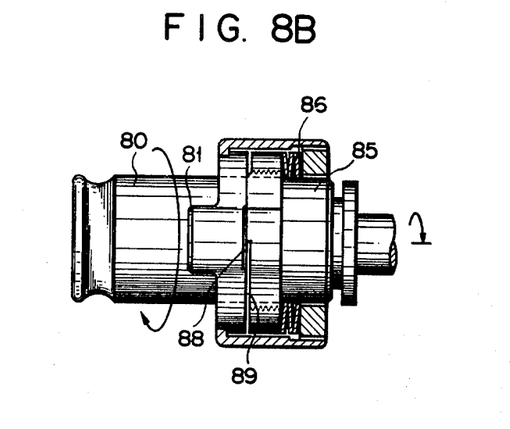

Still further, such a torque limiter as shown in FIG. 8A may be used according to the present invention. This torque limiter different from the torque limiter of FIG. 2 in that a projection 83 of a retainer 82 is fitted in a groove 81 cut in the end of a spindle head 80. A clutch member 85 is disposed in a hollow cylindrical portion of the retainer 82. The clutch member 85 comprises a large-diameter portion and a small-diameter portion. Coned disc springs 86 and a spring force adjusting nut 87 are mounted on the small-diameter portion of the clutch member 85. A groove 88 is cut in that surface of the retainer 82 which faces the large-diameter portion of the clutch member 85. A projection 89 is formed on the surface of the large-diameter portion of the clutch member 85. The projection 89 is inserted in the groove 88 as long as an ordinary load is applied on a drill (not shown) attached to the clutch member 85. When the drill is overloaded, the projection 89 slips out of the groove 88, as shown in FIG. 8B. In this condition, the clutch member 85 slips on the retainer 82 in spite of the friction between it and the retainer 82. Hence, the drill is no longer overloaded. As the spindle head 80 further rotates, the projection 89 is pushed into the groove 88 by the coned disc springs 86, thus generating high-level elastic waves.

What is claimed is:
 1. A device for detecting tool abnormality, comprising:
   coupling means coupled between a tool holder and a rotatable main spindle for normally transmitting rotation of the main spindle to the tool holder, and for repeatedly stopping the transmission of rotation of the main spindle to the tool holder only when a tool abnormality exists, thereby generating elastic waves of a predetermined level;
   a transducer for converting the elastic waves into an electrical signal; and
   an amplitude discriminator for generating an output signal when the output signal from the transducer surpasses a threshold value.
 2. A device according to claim 1, wherein said coupling means has a torque limiter which comprises a bottomed hollow cylindrical retainer coupled to said main spindle and having at least one ball-receiving hole cut in the bottom, a driver coupled to said tool holder, a disc fixed to the driver having at least one ball-receiving recess, a ball disposed partly in the ball-receiving hole and partly in the ball-receiving recess, a guide bush for pushing the ball into the ball-receiving recess and a plurality of coned disc springs mounted on the guide bush.

3. A device according to claim 1, wherein said coupling means has a torque limiter which comprises a tooling section coupled to said main spindle, a leaf spring attached to the inner surface of the tooling section, a ratchet fixed to the leaf spring and a plurality of triangular teeth formed on the outer periphery of said tool holder inserted in the tooling section and being capable of engaging with the ratchet.

4. A device according to claim 1, further comprising alarm means coupled to said amplitude discriminator for generating an alarm when the output signal from the transducer surpasses said threshold value.

5. A device according to claim 4, further comprising a controller for stopping operation of the tool responsive to said output signal of said amplitude discriminator.

6. A device according to claim 1, further comprising a controller for stopping operation of the tool responsive to said output signal of said amplitude discriminator.

7. A device according to claim 1, wherein said tool is a rotary tool mounted in said tool holder.

* * * * *